United States Patent
Miller et al.

(10) Patent No.: US 7,567,831 B2
(45) Date of Patent: Jul. 28, 2009

(54) RESPIRATORY MEASUREMENT SYSTEM AND METHOD RELATED THERETO

(75) Inventors: Michael Ronald Miller, Waukesha, WI (US); Elizabeth Ann Thottakara, Niagara, WI (US); Phil E. Pearson, Jr., Hartland, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 273 days.

(21) Appl. No.: 10/707,775

(22) Filed: Jan. 12, 2004

(65) Prior Publication Data

US 2005/0171417 A1 Aug. 4, 2005

(51) Int. Cl.
*A61B 5/05* (2006.01)

(52) U.S. Cl. ............... 600/407; 600/529; 600/538; 600/534; 600/536; 600/593; 600/595; 128/200.24; 378/8; 378/62

(58) Field of Classification Search ............... 600/407, 600/529, 538, 534, 593, 595, 536; 128/653, 128/200.24, 203.28; 378/8, 62

See application file for complete search history.

(56) References Cited

U.S. PATENT DOCUMENTS

| | | | |
|---|---|---|---|
| 3,759,249 A | | 9/1973 | Fletcher et al. |
| 4,308,872 A | * | 1/1982 | Watson et al. ............... 600/538 |
| 4,878,499 A | * | 11/1989 | Suzuki et al. ............... 600/410 |
| 5,067,494 A | | 11/1991 | Rienmueller et al. |
| 5,207,230 A | * | 5/1993 | Bowers ...................... 600/593 |
| 5,235,989 A | * | 8/1993 | Zomer ........................ 600/534 |
| 5,555,880 A | | 9/1996 | Winter et al. |
| 6,298,260 B1 | * | 10/2001 | Sontag et al. ............... 600/413 |
| 6,597,939 B1 | * | 7/2003 | Lampotang et al. ......... 600/427 |
| 6,740,046 B2 | * | 5/2004 | Knapp et al. ................ 600/538 |
| 6,865,248 B1 | * | 3/2005 | Rasche et al. ................. 378/8 |
| 2006/0087325 A1 | * | 4/2006 | Ariav et al. .................. 324/637 |

* cited by examiner

*Primary Examiner*—Brian Casler
*Assistant Examiner*—John F Ramirez
(74) *Attorney, Agent, or Firm*—Cantor Colburn LLP

(57) ABSTRACT

A respiratory measurement system and a method for measuring respiratory motion are provided. The system includes a strapping device that is configured to be placed across a chest of a person. The strapping device is substantially transparent to x-rays. The system further includes a sensor operatively coupled to the strapping device generating a measurement signal indicative of a displacement of the strapping device during respiration by the person.

5 Claims, 5 Drawing Sheets

US 7,567,831 B2

RESPIRATORY MEASUREMENT SYSTEM AND METHOD RELATED THERETO

BACKGROUND OF INVENTION

The invention relates to a respiratory measurement system and a method for measuring respiratory motion of a person.

Respiratory measurement systems have been provided to provide visual feedback or biofeedback relating to a person's respiration. Further, respiratory measurement systems may be used in conjunction with medical imaging devices such as x-ray devices. In a respiratory measurement system, an air bellows is placed around a person's chest when they are lying on an x-ray table. During respiration by the person, the pressure is the air bellows varies and the pressure variation is detected by a pressure transducer. The pressure transducer generates a signal based on the pressure variation.

The inventors herein have recognized that the system has several drawbacks. In particular, the air bellows of the system is not transparent to x-rays and thus an image of the air bellows is undesirably obtained on the x-ray image of a person. Thus, the inventors have recognized that there is a need for a respiratory measurement system that will be substantially transparent to x-rays.

SUMMARY OF INVENTION

The foregoing problems and disadvantages are overcome by a respiratory measurement system and a method for measuring respiratory motion of a person as described herein.

A respiratory measurement system in accordance with a first embodiment of the invention is provided. The system includes a strapping device that is configured to be placed across a chest of a person. The strapping device is substantially transparent to x-rays. The system further includes a sensor operatively coupled to the strapping device generating a measurement signal indicative of a displacement of the strapping device during respiration by the person.

A medical diagnostic system in accordance with a second embodiment of the invention is also provided. The medical diagnostic system includes a tabletop and an x-ray device disposed proximate the tabletop. The system further includes a strapping device that is configured to be placed across a chest of a person lying on the tabletop. The strapping device is substantially transparent to x-rays. The system further includes a sensor operatively coupled to the strapping device generating a measurement signal indicative of a displacement of the strapping device during respiration by the person. The sensor is disposed outside of a scanning area of the x-ray device.

A method for measuring respiratory motion of a person in accordance with a third embodiment of the invention is provided. The method includes disposing a strapping device across a chest of a person. The strapping device is substantially transparent to x-rays. The method further includes generating a measurement signal indicative of a displacement of the strapping device during respiration by the person.

DETAILED DESCRIPTION

Figure 1:
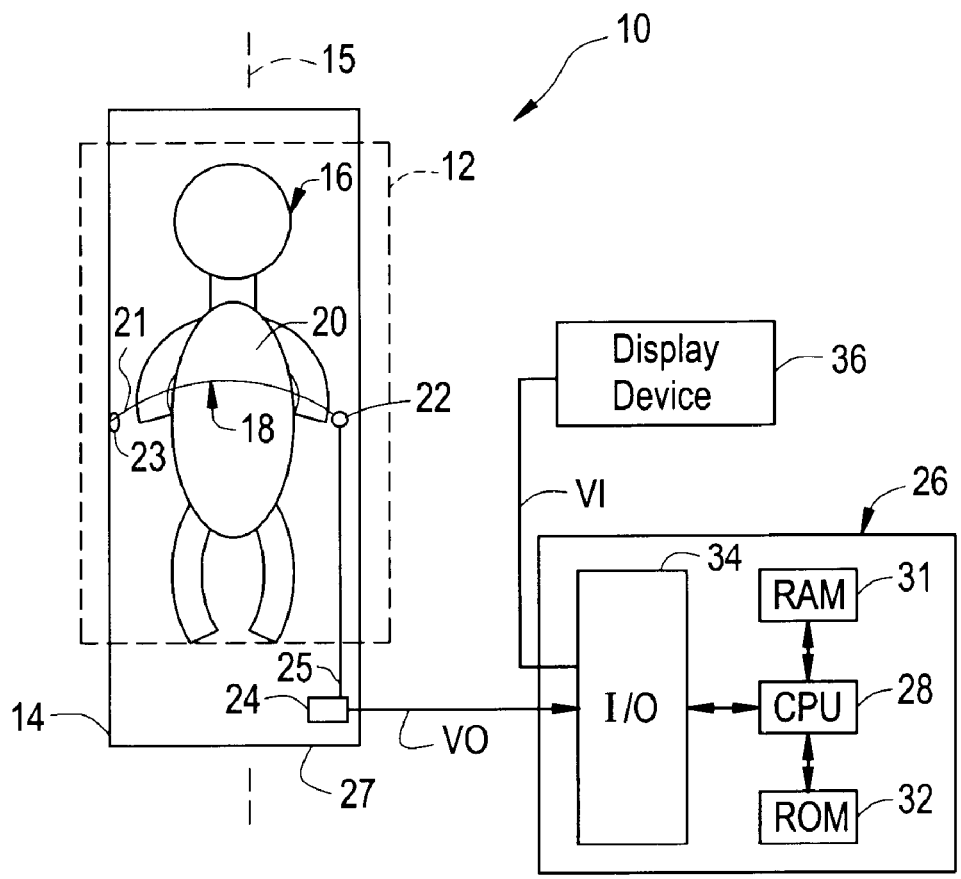
FIG. 1 is a block diagram of a respiratory measurement system and a conventional x-ray device.
Figure 2:
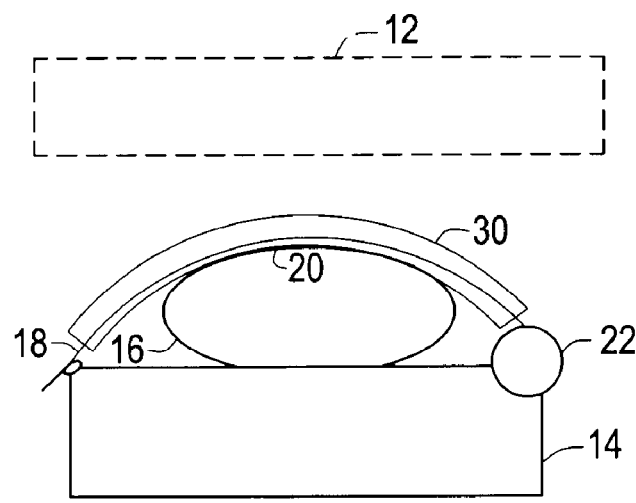
FIG. 2 is a side view of the respiratory measurement system and x-ray device of FIG. 1.

Referring to the drawings, identical reference numerals represent identical components in the various views. Referring to FIGS. 1 and 2, a respiratory measurement system 10 may include a tabletop 14, a plastic string 18, a string holder 23, a pulley 22, a linear position sensor 24, a computer 26, and a display device 36. System 10 may further include a plastic tube 30 and an x-ray device 12. While embodiments described herein depict a plastic string 18 as a particular strapping device, it will be appreciated that other materials and strapping configurations may be employed for use in embodiments of the invention, where the material is substantially transparent to x-rays.

Tabletop 14 is provided to hold a person 16 thereon. Tabletop 14 may rest on rollers (not shown) to allow table 14 to be slidably moved along axis 15.

Plastic string or cord 18 is provided to allow measurement of the respiration of person 16. In particular, string 18 may be fixedly attached to string holder 23 and then disposed across a portion of a chest 20 of person 16 to pulley 22. From pulley 22, string 18 may further extend to the linear position sensor 24. Plastic string 18 may be constructed from any material that is substantially transparent to x-rays so that string 18 will not be displayed on an x-ray image produced by x-ray device 12. For example, string 18 may be constructed from polypropylene. String holder or string securing device 23 is provided to hold an end of string 18 to a first side of tabletop 14. String holder 23 may comprise a string clamp or other means for holding a string for example. String holder 23 may be constructed from any material that is substantially transparent to x-rays so that holder 23 will not be displayed on an x-ray image produced by x-ray device 12. For example, string holder 23 may be constructed from polypropylene.

Pulley 22 is conventional in the art and may be fixedly attached to tabletop 14. Pulley 22 may be constructed from any material that is substantially transparent to x-rays so that pulley 22 will not be displayed on an x-ray image produced by x-ray device 12. For example, pulley 22 may be constructed from polypropylene. As shown, pulley 22 is preferably disposed on a second side of tabletop 14 opposite string holder 23.

Referring to FIG. 2, tube 30 may be provided to allow string 18 to move during respiration of person 16 with minimal friction. As shown, tube 30 may be disposed across a portion of chest 20 of person 16. Further, string 18 may be disposed within tube 30 between string holder 23 and pulley 22. Tube 30 may be constructed from any material that is substantially transparent to x-rays so that tube 30 will not be displayed on an x-ray image produced by x-ray device 12.

Referring to FIG. 1, linear sensor 24 may comprise any sensor capable of determining a linear displacement of an end of string 18. For example, sensor 24 may comprise one of a plurality of linear position encoders including, for example, an analog encoder or a quadrature encoder. In particular, encoder 24 may generate a signal (VO) directly indicative of the linear position of an end 25 of string 18 and indirectly indicative of a lung volume level of person 16 during respiration. As shown, encoder 24 is preferably disposed outside of the scanning area of x-ray device 12. For example, encoder 24 may be disposed proximate an end 27 of tabletop 14.

During respiration or breathing (i.e., inhaling and exhaling air) by person 16, the position of an end 25 of string 18 will vary because an end 21 of string 16 is at a fixed location. The linear position encoder 24 can measure the linear displacement of string 18 and generate a signal (VO) indicative of the respiration of person 16. In particular, the signal (VO) is indicative of the lung volume level of person 16.

Computer 26 is provided to receive signal (VO) from encoder 24 and to generate a display signal (V1) based on signal (VO) for providing respiration biofeedback to person 16. Computer 26 includes a microprocessor 28 communicating with various computer readable storage medium. The computer readable storage media preferably includes non-volatile and volatile storage in a read-only memory (ROM) 32 and a random access memory (RAM) 31. The computer readable medium may be implemented using any of a number of memory devices such as PROMs, EPROMs, EEPROMS, flash memory or any other electric, magnetic, optical or combination memory device capable of storing data, some of which represent executable instructions used by microprocessor 28. Microprocessor 28 may transmit signal (V1) to display device 36 via an input/output (I/O) interface 34.

Figure 3:
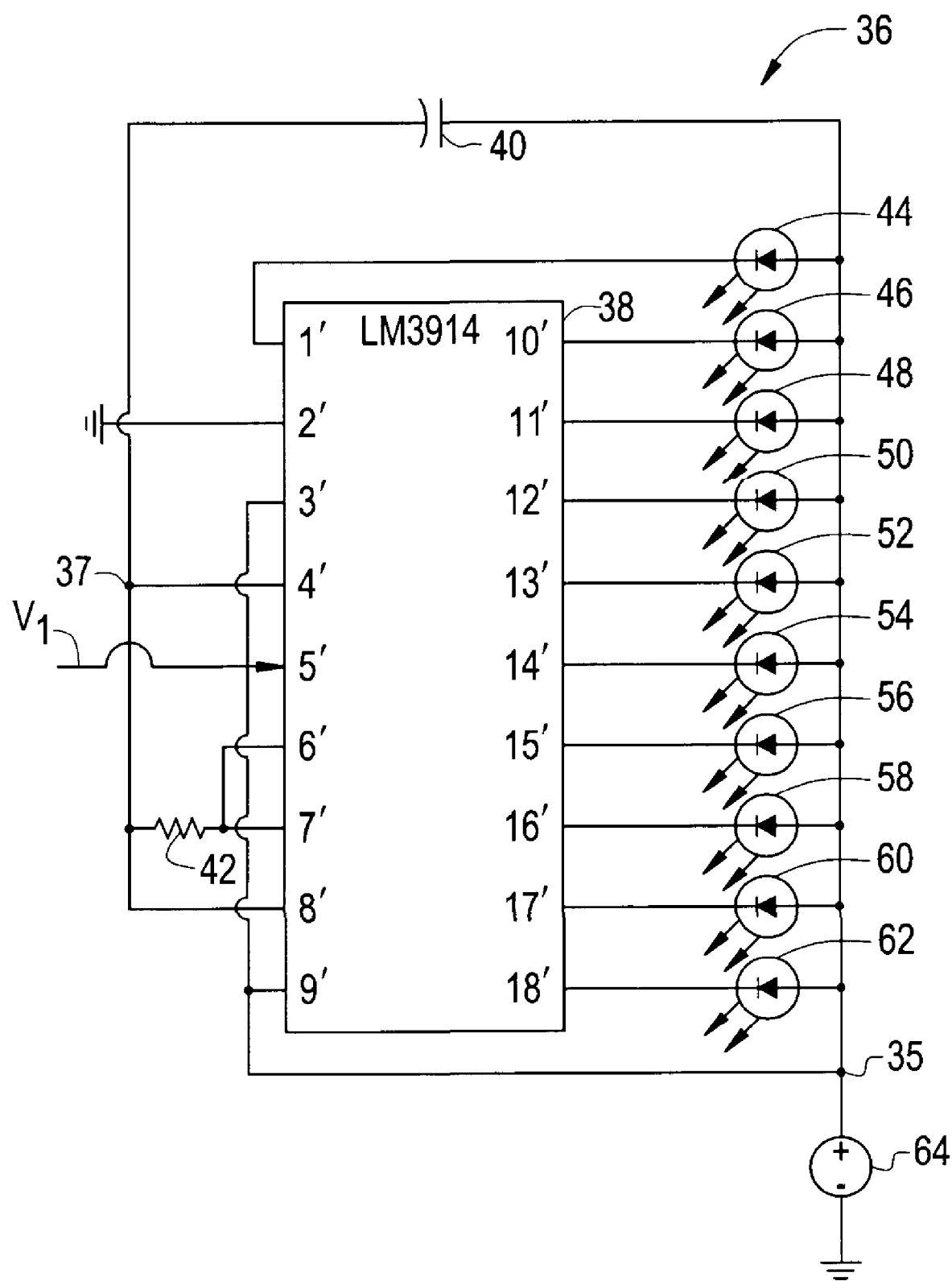
FIG. 3 is a circuit schematic of the display device shown in FIG. 1.

Display device 36 provides visual biofeedback information to person 16. In particular, display device 36 receives signal (V1) from computer 26 and illuminate light emitting diodes (LEDs) based on signal (V1). Referring to FIG. 3, a detailed schematic of an exemplary embodiment of device 36 is illustrated. As shown, device 36 may comprise include a LED driver chip 38 that comprises chip LM3914 manufactured by National Semiconductor for example. As shown, driver chip 38 may be coupled to LEDs 44, 46, 48, 50, 52, 54, 56, 58, 60, 62 at output pins 1', 10', 11', 12', 13', 14', 15', 16', 17', 18', respectively. Further, the LEDs 44-62 may be further coupled to voltage source 64 a node 35. Further, device 36 may include a capacitor coupled between at node 35 and a node 37. Pin 7' of chip 38 may be coupled through a resistor 42 to node 37 and pin 8' may be directly coupled to node 37. Pins 3', 9' of chip 38 may be directly coupled to node 35.

As shown, chip 38 receives a signal (V1) from computer 26 and may energize one or more of LEDs 44-62 based on an amplitude of signal (V1). For example, when signal (V1) corresponds to a minimum lung volume level of person 16, chip 38 may energize one LED, such as LED 44. Further, when signal (V1) corresponds to a maximum lung volume level of person 16, chip 38 may energize LEDs 44-62.

Figure 4A:
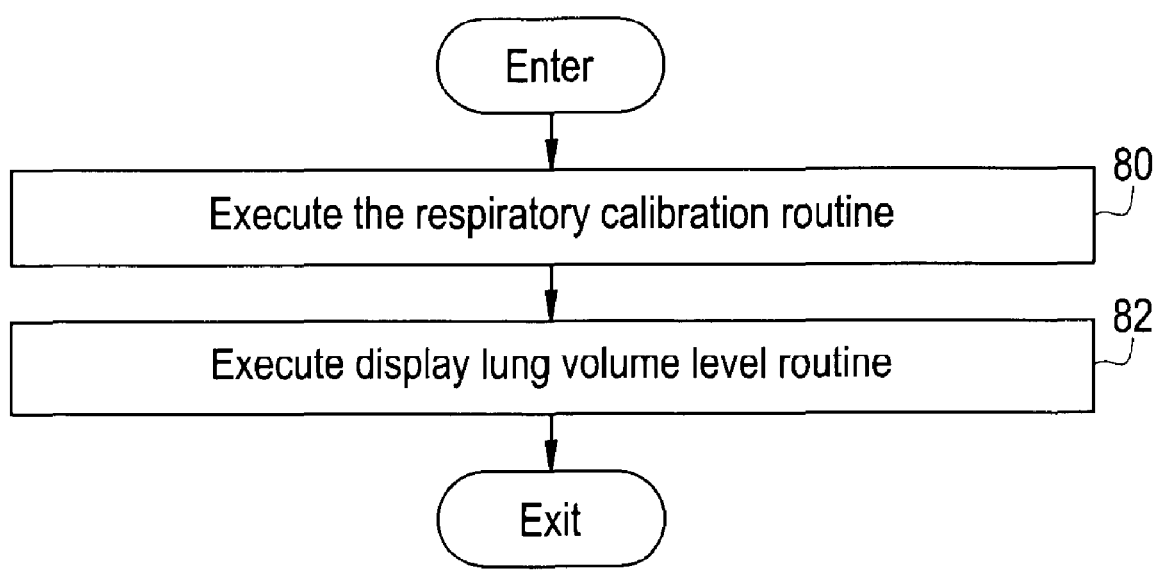
FIGS. 4A-4C are flowcharts of a method for measuring respiratory motion of a person.
Figure 4B:
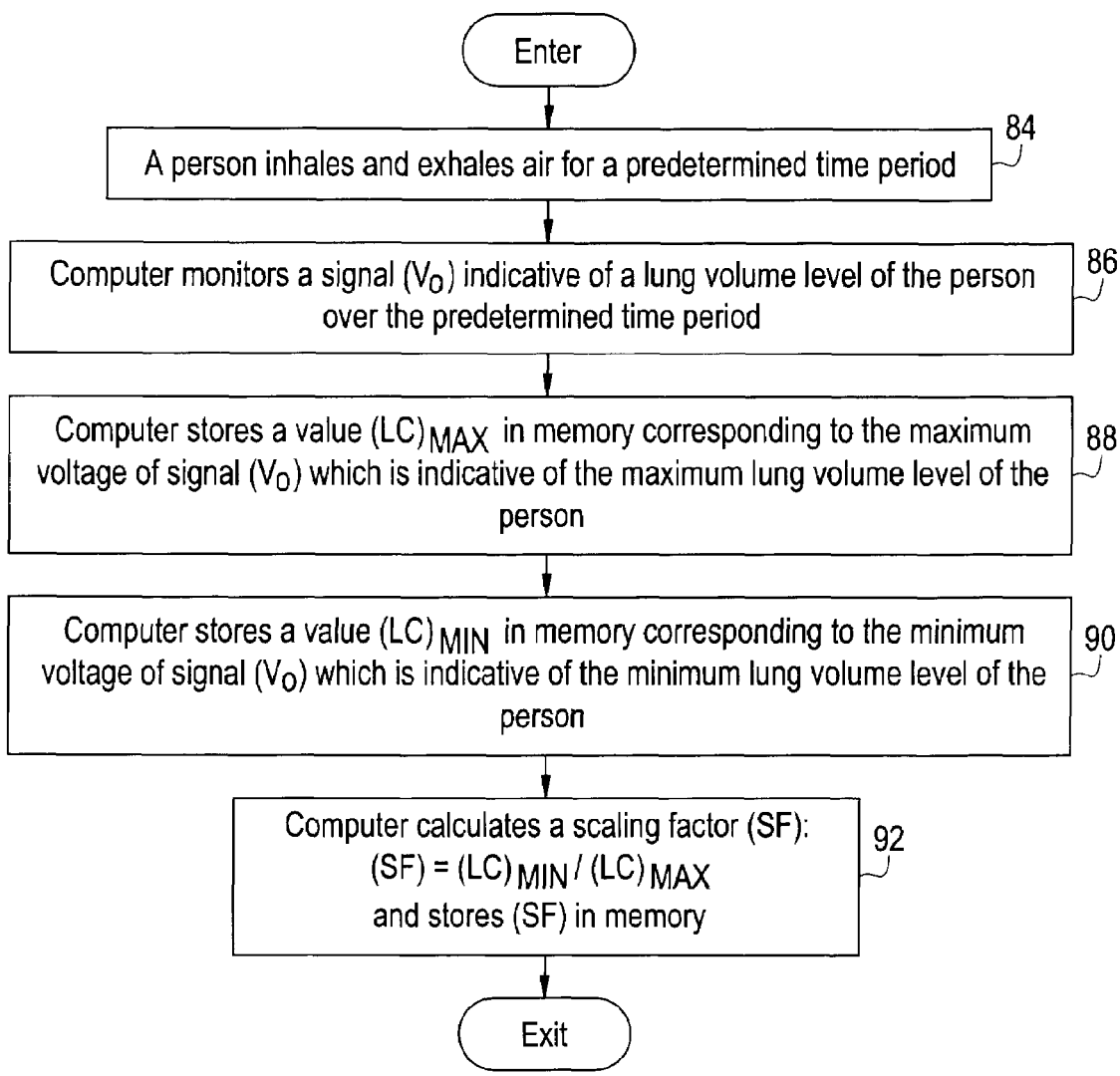
Figure 4C:
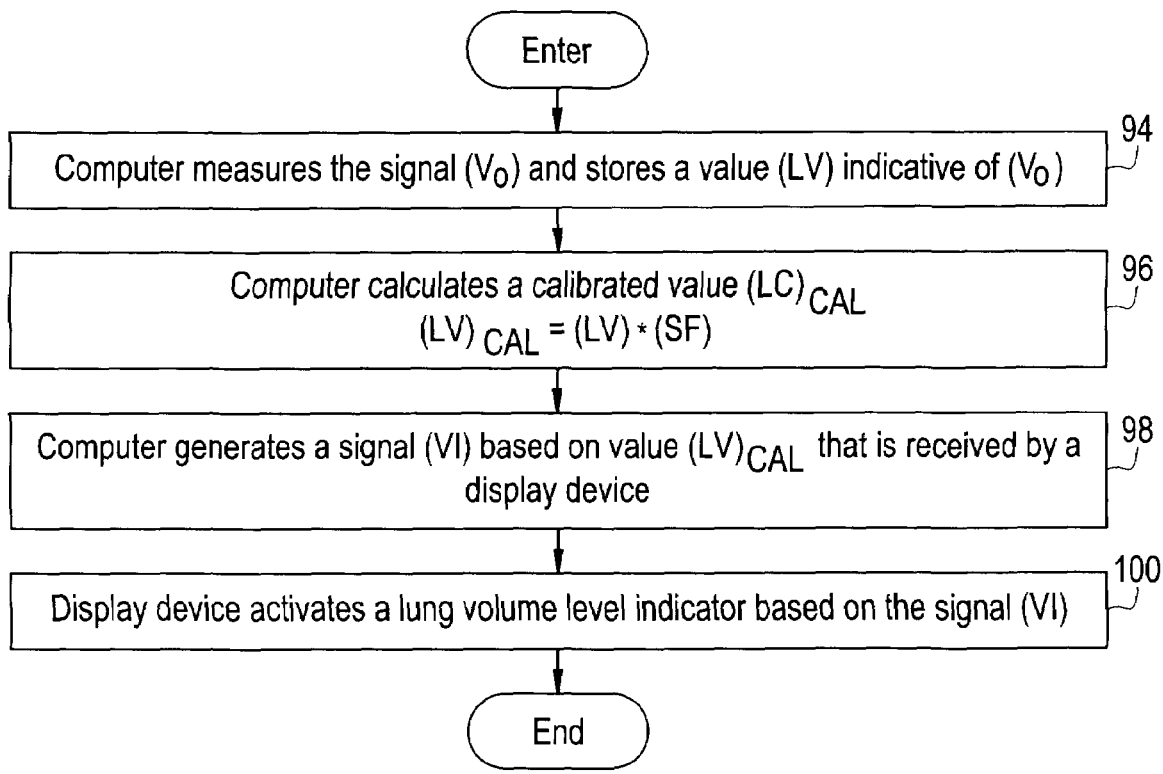

Referring to FIGS. 4A-4C, a method for measuring respiratory motion of a person will now be explained. In particular, the method may be implemented in part by software stored in ROM 32 or RAM 31 and executed in microprocessor 28 of computer 26.

At step 80, computer 26 executes the "respiratory calibration routine". Referring to FIG. 4B, the "respiratory calibration routine" includes steps 84-94. At step 84, person 16 inhales and exhales air for a predetermined time.

Next at step 86, computer 26 monitors a signal (VO) indicative of a lung volume level of person 16 over the predetermined time period.

Next at step 88, computer 26 stores a value (LV)MAX in memory corresponding to the maximum voltage of signal (VO) that is indicative of the maximum lung volume level of person 16 over the predetermined time period.

Next at step 90, computer 26 stores a value (LV)MIN in memory corresponding to the minimum voltage or count of signal (VO) that is indicative of the minimum lung volume level of person 16.

Next at step 92, computer 26 calculates a scaling factor (SF) that will be used by computer 26 to scale respiratory biofeedback information provided to person 16 based on the lung capacity of person 16. In particular, computer 26 calculates the scaling factor (SF) utilizing the following equation: (SF)=(LV)MIN/(LV)MAX.

After step 92, the method advances to step 82. At step 82, computer 26 executes the "display lung volume level" routine. The "display lung volume level" routine is implemented in steps 94-100. At step 94, computer 26 measures the signal (VO) utilizing I/O interface 34 and stores a measurement value (LV) indicative of signal (VO) (which is indicative of a current lung volume level of person 16) in memory.

At step 96, computer 26 calculates a calibrated lung volume level value (LV)CAL indicative of a lung volume level relative to lung volume range of person 16.

Next at step 98, computer generates an output signal (V1) based on value (LV)CAL that is received by display device 36.

Next at step 100, display device 36 provides a visual indication of respiratory function (e.g., lung volume level) based on the signal (V1). For example, display device 36 may illuminate LED 44, when signal (V1) corresponds to a minimum predetermined voltage level. Alternately, display device 36 may illuminate LEDs 44-62 when signal (V1) corresponds to a maximum predetermined voltage level. After step 100, the routine is exited.

The respiratory measurement system and method related thereto provide a substantial advantage over other systems and methods. In particular, the system and method allows the measurement of respiratory function (e.g., lung volume level) utilizing a plastic string that is substantially transparent to x-rays. Thus, the respiratory measurement system can be utilized in conjunction with x-ray devices without having components of the system being displayed in x-ray images generated by x-ray devices.

While embodiments of the invention is described with reference to an exemplary embodiments, it will be understood by those skilled in the art that various changes may be made an equivalence may be substituted for elements thereof without departing from the scope of the invention. In addition, many modifications may be made to the teachings of the invention to adapt to a particular situation without departing from the scope thereof. Therefore, is intended that the invention not be limited the embodiment disclosed for carrying out this invention, but that the invention includes all embodiments falling with the scope of the intended claims. Moreover, the use of the term's first, second, etc. does not denote any order of importance, but rather the term's first, second, etc. are us are used to distinguish one element from another.

The invention claimed is:

1. A respiratory measurement system, comprising:
a plastic tube configured to be placed across a chest of the person, the plastic tube being substantially transparent to x-rays;
a plastic cord having a portion that is disposed through an interior of the plastic tube, the plastic cord being substantially transparent to x-rays;
a linear position sensor coupled to an end of the plastic cord, the end of the plastic cord being configured to be disposed away from the chest of the person, the linear position sensor generating a measurement signal indicative of an amount of linear displacement of the plastic cord during respiration by the person; and
a tabletop having a securing device and a pulley coupled thereto, wherein a first portion of the plastic cord extends between the securing device and the pulley, the securing device and the pulley being positioned on the tabletop to allow the chest of the person to be disposed between the securing device and the pulley.

2. The respiratory measurement system of claim 1 wherein a second portion of the plastic cord extends from the pulley to the linear position sensor.

3. A medical diagnostic system, comprising:
 a tabletop;
 an X-ray device disposed proximate the tabletop;
 a plastic cord that has a portion configured to be placed across a chest of a person lying on the tabletop, the plastic cord being substantially transparent to x-rays;
 a linear position encoder operatively coupled to an end of the plastic cord generating a measurement signal indicative of an amount of displacement of the plastic cord during respiration by the person, the end of the plastic cord and the linear position encoder being configured to be disposed away from the chest of the person outside a scanning area of the X-ray device; and
 a securing device and a pulley coupled to the tabletop, a first portion of the plastic cord extending between the securing device and the pulley, the securing device and the pulley being positioned on the tabletop to allow a chest of the person to be disposed between the securing device and the pulley.

4. A respiratory measurement system, comprising:
 a plastic cord that is configured to be placed across a chest of a person, the plastic cord being substantially transparent to x-rays;
 a sensor coupled to the plastic cord generating a measurement signal indicative of an amount of displacement of the plastic cord during respiration by the person; and
 a tabletop having a securing device and a pulley coupled thereto, wherein a first portion of the plastic cord extends between the securing device and the pulley, the securing device and the pulley being positioned on the tabletop to allow the chest of the person to be disposed between the securing device and the pulley.

5. A medical diagnostic system, comprising:
 a tabletop;
 an X-ray device disposed proximate the tabletop;
 a plastic cord that is configured to be placed across a chest of a person lying on the tabletop, the plastic cord being substantially transparent to x-rays;
 a sensor operatively coupled to the plastic cord generating a measurement signal indicative of an amount of displacement of the plastic cord during respiration by the person, the sensor being outside a scanning area of the X-ray device; and
 a securing device and a pulley coupled to the tabletop, a first portion of the plastic cord extending between the securing device and the pulley, the securing device and the pulley being positioned on the tabletop to allow the chest of the person to be disposed between the securing device and the pulley.

* * * * *